US006825378B2

(12) United States Patent
Kumar et al.

(10) Patent No.: US 6,825,378 B2
(45) Date of Patent: Nov. 30, 2004

(54) PROCESS FOR THE SYNTHESIS OF ENANTIOMERICALLY PURE CYCLOHEXYLPHENYL GLYCOLIC ACID

(75) Inventors: Pradeep Kumar, Maharashtra (IN); Rodney Agustinho Fernandes, Maharashtra (IN); Priti Gupta, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/400,653

(22) Filed: Mar. 28, 2003

(65) Prior Publication Data

US 2004/0192962 A1 Sep. 30, 2004

(51) Int. Cl.[7] ............................................ C07C 57/030
(52) U.S. Cl. ....................... 562/489; 562/470; 562/491
(58) Field of Search ................................. 562/489, 470, 562/491, 468

(56) References Cited

U.S. PATENT DOCUMENTS 6,025,177 A * 2/2000 Senanayake et al. ........ 435/195
6,140,529 A * 10/2000 Bakale et al. ................. 560/58

* cited by examiner

*Primary Examiner*—Rita Desai
*Assistant Examiner*—Hector M. Reyes
(74) *Attorney, Agent, or Firm*—Oliff & Berridge, PLC

(57) ABSTRACT

The present invention provides a process for the synthesis of enantiomerically pure cyclohexylphenyl glycolic acid of formula (1). The present invention more particularly relates to a process using cyclohexylphenyl ketone for the synthesis of enantiomerically pure cyclohexylphenyl glycolic acid of formula (1).

18 Claims, No Drawings

PROCESS FOR THE SYNTHESIS OF ENANTIOMERICALLY PURE CYCLOHEXYLPHENYL GLYCOLIC ACID

FIELD OF INVENTION

The present invention relates to a improved process for the synthesis of enantiomerically pure cyclohexylphenyl glycolic acid of formula (1). The present invention more particularly relates to a process using cyclohexylphenyl ketone for the synthesis of enantiomerically pure cyclohexylphenyl glycolic acid of formula (1)

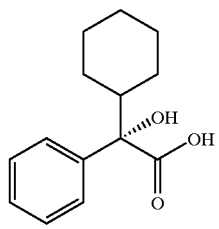

Formula (1)

BACKGROUND ART

Tertiary hydroxy acids/esters are highly important intermediates in the synthesis of a variety of medicinal agents [(a) Carter, P. J.; Blob, L; Audia, V. A.; Dupont, A. C.; Mcpherson, D. W.; NataleJr, K J.; Reszotarski, W. 1.: Spadguolo, C. J.; Waid, P P.; Kaicer, C. Med. Chem. 1991, 34, 3065; (b) Tambutc, A.; Collet, A. Butll De La Chimi. Fr. 19&4, -2,11-77; (c) Kiesewetter, D. O. Tetrahedron: Asymmetry 19.93, 4, 2183; (d)McPherson, D. W.; Knapp, F. F. J. Org. Chem. 1996, 61, 8335] and natural products [(a) Caldwell, C. G.; Riupprecht, K. M; Bondy, S. S.; Pavis, A. A. J. Org. Chemt. 1990, 55, 2355; (b) Kada4 Y.; Fukuyamai T. J. Am. Chem. Soc. 1993, 115, 8451]. Cyclbhexylphenyl glycolic acid is an important intermediate for the synthesis of oxybutynin (Ditropan), which is a widely prescribed muscaronic receptor antagonist for the treatment of urinary frequency; urgency and urge incontinence Yarker. Y. E.; Goa, K. L.; Fitton, A. Drug Aging, 1995, 6, 243.

In the prior-art the synthesis of cyclohexylphenyl glycolic acid segment of oxybutynin and related tertiary hydroxy esters has been accomplished employing various synthetic strategies.

An early synthesis utilizes carbohydrate systems containing an asymmetric benzylic center of known absolute configuration, which on degradation give tertiary hydroxy acids in enantiomerically pure form [Inch, T. D.; Ley, R Rich, P. J. Chem. Soc. ©, 1968, 1693.

In another prior art method, cis-aminoindanol or related constrained amino alcohols are used as a highly defined chiral handle for the preparation of enantiopure tertiary α-hydroxy acids via appropriate metal coordinated 1,1-dicarbonyl systems in the Grignard reaction to give tertiary hydroxy acids in 99% enantiomeric purity [Senanayake, C. H.; Fang, K; Grover, P.; Bakale, R. P.; Vandenbossche, C. P.; Wald, S. A. Tetrahedron Lett. 0.1999, 40, 819].

In yet another prior art method chiral mandelic acid has been used as a template to generate the tertiary hydroxy acid by Aldol process to give cyclohexylphenyl glycolic acid it greater than 99.9% diasteromeric purity [Grover, P. T.; BHongle, Nr. N.; Wald, S. A.; Senamayake, C. H. J. Org Chem. 2000, 65, 6283]

In still another prior art method the racemic cyclohexylphenyl glycolic acid is resolves via the tyrosine methyl ester to further obtain the cyclohexylphenyl glycolic acid in 99% enantiomeric purity [(a) Bakale, et al. US 6140529, 2000; (b) US S973182, 1998]. Some of the major drawbacks of the methods known in the prior-art are such as follows:

(i) Multi-step synthesis
(ii) High cost of chiral materials employed
(iii) Complicated reagents and longer reaction time:
(iv) Difficulties involved in work-up procedure:
(v) Overall low yield of the desired compound;
(vi) Lack of reusability of expensive reagents

OBJECTS OF THE INVENTION

The main object of the present invention is to develop an improved, efficient and enantio selective process for the synthesis of cyclohexylphenyl glycolic acid.

An object of the present invention is, to provide a process for the synthesis of enantiomerically pure cyclohexylphenyl glycolic acid, which overcomes the drawbacks of the prior-art processes employing the sharpless asymmetric dihydroxylation and selective oxidation of primary hydroxyl to an acid.

DETAILED DESCRIPTION OF THE INVENTION

Accordingly, the present invention provides a process for the preparation of enantiomerically pure cyclohexylphenyl glycolic acid, said process comprising the steps of:

a) treating cyclohexylphenyl ketone of formula (2)

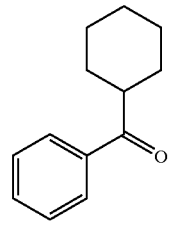

Formula (2)

with an ylide in an anhydrous solvent for a tine period of 4–8 hours at an ambient temperature to obtain α-cyclohexylstyrene of formula (3);

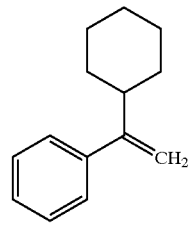

Formula (3)

b) reacting α-cyclohexylstyrene (3) obtained in step (a) with dihydroxylating agents and a chiral ligand, in t-BuOH, at a temperature range of −15° C. to an ambient temperature, for a time period of 12–18 hours, to obtain a chiral dial of formula (4);

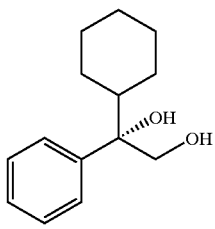

Formula (4)

c) oxidizing the primary hydroxyl group of the chiral diol (4) with: an oxidizing agent in an organic solvent at a temperature range of −80° C. to −50° C. to obtain hydroxy aldehyde; and d) oxidizing the hydroxy aldehyde of step (c) with an oxidizing agent and a buffer to obtain an enantiomerically pure cyclohexylphenyl glycolic acid of formula (1).

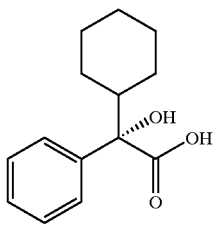

Formula (1)

An embodiment of the present invention, wherein in step (a) the ylide used is generated by reacting methyl triphenylphosphonium iodide or bromide with a base at a temperature in the range of 0° C. to ambient temperature.

Another embodiment of the present invention, wherein in step (a) the base is selected from a group consisting of n-Butyl Lithium, sodium amide, Lithium bis (trimethylsilyl) amide (LiHMDSX), Sodiumbis (trimethylsilyl) amide (NS), Potassium tertiary butoxide (t-BuOK), or Sodium hydride (NaH).

Yet embodiment of the present invention, wherein in step (a) the base is n-butyllithium.

Still another embodiment of the present invention, wherein in step (b) dihydroxylating agent is osmium tetraoxide.

Further embodiment of the present invention, wherein in step (b) the chiral ligand controls the formation of R and S form of chiral diol.

Yet another embodiment of the present invention, wherein the chiral ligand is selected front 1st or $_2$nd generation mono or bidentate ligands.

Further embodiment of the present invention, wherein the chiral ligand is selected from phthalazine, pyrimidine, phenanthryl, quinoxaline, p-chlorobenzoate or anthraquinyl groups.

Still another embodiment of the present invention, wherein the chiral ligand is phthalazine. It is also an embodiment of the present invention, wherein in step (c) oxidizing agent is selected from a group consisting of oxalyl chloride and DMSO, phosphorus pentoxide and DMSO, trifluoroacetic anhydride and DMSO, pyridinium chlorochromate, pyridinium dichromate, 2,2,6,6 tetramethyl 1-piperidinyloxy free radical) TEMPO, or tetra-n-propylammonium perruthenate (TPAP).

Yet another embodiment of the present invention, wherein the oxidizing agent is selected from oxalyl chloride and DMSO or pyridinium chlorochromate.

Still another embodiment of the present invention, wherein in step (d) the buffer is selected from Sodium dihydrogen phosphate and potassium dihydrogen phosphate.

Further embodiment of the present invention, wherein thee oxalyl chloride and DMSO are in the ratio of 1.5:3.0.

Still another embodiment of the present invention wherein in step (c) the organic solvent is selected from chloroform and benzene, Yet another embodiment of the present invention, wherein cyclohexylphenyl glycolic acid can be used to obtain oxybutynin by reaction with 4-N,N-diethylaminobut-2-yn-l-ol in presence of a dehydrating agent or coupling involving the activation of the above acid as mixed anhydride.

Further embodiment of the present invention, wherein for the synthesis of enantiomers of cyclohexylphenyl glycolic acid, a variety of ligands are used in Sharpless asymmetric dihydroxylation.

An improved highly enantioselective synthesis of cyclohexylphenyl glycolic acid has been achieved. The synthetic strategy features a Sharpless asymmetric dihydroxylation (SAD) route to the target compound. The Sharpless asymmetric dihydroxylation of a-cyclohexylstyrene, prepared from cyclohexylphenyl ketone, a readily available starting material gives the optically pure dihydroxy compound (cc>92%). The selective primary hydroxyl oxidation to the corresponding aldehyde and subsequent oxidation to acid furnished cyclohexylphenyl glycolic acid in enatiomerically pure form, a key intermediate in the synthesis of oxybutynin and related derivatives.

The process of the present invention is described herein below with examples, which are illustrative only and should not be construed to limit the scope of present invention in any manner.

Example 1

To a suspension of methyltriphenylphosphonium iodide in dry THF at ambient temperature was added n-BuLi (2M soln in hexane). After stirring for 15 minutes at 0° C. cyclohexylphenyl ketone was added. The reaction mixture was stirred for 8 h at ambient temperature and then quenched with aqueous ammonium chloride and extracted with ethyl acetate. The combined organic phases were washed (brine), dried (Na2SO4) and concentrated. Silica gel column chromatography of the crude product using petroleum ether: EtOAc (49:1) as eluent gave α-cyclohexylstyrene as a colorless oil.

To a mixture of $K_3Fe(CN)_6$, K2CO3 and Hydroquiniel, 4,-phthalazinediyldiether (DHQ)2PHAL in t-BuOH—$H_2O$ (1:1) cooled to 0° C. was added OsO4 (0.1M solution in toluene). After stirring for 5 minutes at 0° C. α-cyclohexylstyrene was added in one portion. The reaction mixture was stirred at 0° C. for 18 b and then quenched with solid sodium sulfite. The stirring was continued for 1 h and the solution was extracted with ethyl acetate. The combined organic phases were washed (brine), dried ($Na_2SO_4$) and concentrated Silica gel column chromatography of crude product using petroleum ether:EtOAc (4:1) as eluent gave (S)-1-cyclohexyl-1-phenyl-1,2-ethanediol as a white solid.

To a solution: of oxalyl chloride in dry dichloromethane cooled at −78° C. was added dry DMSO in dichloromethane and stirred for 20 min. The solution of (S)-1cyclohexyl-1-phenyl-1,2-ethanediol in dichloromethane was added at −60° C. and stirred for 30 min. A solution of triethylamine in dichloromethane was added and stirred for 1.h. The reaction was allowed to warm to ambient temperature and poured into 2N HC1 and extracted with dichloromethane. The combined organic layers were washed (brine), dried ($Na_2SO_4$) and concentrated to give the virtually pure aldehyde as a pale yellow solid.

To the solution of above aldehyde in t-BuOH at. 0° C. was added an aqueous solution of $NaClO_2$ and $NaH_2PO_4.2H_2O$. The yellow solution was stirred at ambient temperature for 4 b and then quenched with solid $Na_2SO_3$. The reaction mixture was acidified with HCl and extracted with dichloromethane. The combined organic phases were washed brine), dried (Na2SO4) and concentrated Silica gel column chromatography of the crude acid with chloroform:MeOH (9:1) gave the (S)-cyclohexylphenyl glycolic acid as a white solid. This was recrystallized from petroleum ether:ether.

Example 2

To a suspension of methylbiphenylphosphonium iodide in dry THF cooled at 0° C. was added NaNH2. After stirring for 15 h at ambient temperature, cyclohexylphenyl ketone Was added. The reaction mixture was stirred for 8 h at ambient temperature and then quenched with aqueous ammonium chloride and extracted with ethyl acetate. The combined organic phases were washed (brine), dried ($Na_2SO_4$) and concentrated. Silica gel column chromatography of the crude product using petroleum ether:EtOAc (49:1) as eluent gave α-cyclohexylstyrene as a colorless oil.

To a mixture of $K_3Fe(CN)_6$, $K_2CO_3$ and $(DHQ)_2PHAL$ in t-BuOH:$H_2O$ (1:1) cooled to −15° C. was added $OsO_4$ (0.1M solution in toluene). After string for 5 minutes at 0° C., α-cyclohexyl styrene was added in one portion. The reaction mixture was stirred at 0° C. for 18h and then quenched with solid sodium sulfite. The string was continued for 1 h and the solution was extracted with ethyl acetate. The combined organic-phases were washed (brine), dried ($Na_2SO_4$) and concentrated. Silica gel column chromatography of crude product using petroleum ether:EtOAc (4:1) as eluent gave (S)-1-cyclohexyl-1-phenyl-1,2-ethanediol as a white solid.

To a suspension of phosphorus pentoxide in dry dichloromethane cooled at 0° C. was added dry DMSO in dichloromethane and stirred for 20 min. The solution of (S)-1cyclohexyl-1-phenyl-1,2-ethanediol in dichloromethane was added at 0° C. and stirred for 30 min. A solution of triethylamine in dichloromethane was added and stirred for 1 h. The reaction was allowed to warm to ambient temperature and poured into 2N HCl and extracted with dichloromethane. The combined organic layers were washed (brine), dried (Na2SO4) and concentrated to give the virtually pure aldehyde as a pale yellow solid.

To the solution of above aldehyde in t-BuOH at 0° C. was added an aqueous solution of $KClO_2$ and $NaH_2PO_4.2H_2O$. The yellow solution was stirred at ambient temperature for 4 h and then quenched with solid $Na_2SO_3$. The reaction mixture was acidified with HCl and extracted with dichloromethane. The combined organic phases were washed, (brine), dried ($Na_2SO_4$) and concentrated. Silica gel column chromatography of the crude acid with chloroform:MeOH (9:1) gave the (S)-cyclohexylphenyl glycolic acid as a white solid. This was recrystallized from petroleum ether:ether.

Example 3

To a suspension of methyltriphenylphosphonium iodide in dry THF cooled at 0° C. was added NaHMDS (1M soln in THE). After stirring for 15 minutes at 0° C., cyclohexylphenyl ketone was added in one portion. The reaction mixture was stirred for 8 h at ambient temperature and then quenched with aqueous ammonium chloride and extracted with ethyl acetate. The combined organic phases were washed (brine), dried ($Na_2SO_4$, and concentrated. Silica gel column chromatography of the crude product using petroleum ether: EtOAc(49:1) as eluent gave α-cyclohexylstyrene as a colorless oil.

To a mixture of $K_3Fe(CN)_6$, K2CO3 and (DHQ)2PHAL in t-BuOH—$H_2O$ (1:1) at ambient temperature was added OsO4 (0.1M solution in toluene). After stirring for 5minutes at 0° C., α-cyclohexylstyrene was added in one portion. The reaction mixture was stirred at 0° C. for 18 h and then quenched with solid sodium sulfite. The stirring was continued for 1 h and the solution was extracted with ethyl acetate. The combined organic phases were washed (brine), dried ($Na_2SO_4$) and concentrated. Silica gel column chromatography of crude product using petroleum ether:EtOAc (4:1) as eluent gave (S) 1-cyclohexyl-1-phenyl-1, 2ethanediol as a white solid.

To a solution of trifluroacetic anhydride in dry dichloromethane cooled at −78° C. was added dry DMSO in dichloromethane and stirred for 20 min. The solution of (S)-1 cyclohexyl-1phenyl-1,2-ethanediol in dichloromethane was added at −60° C. and stirred for 30 min. A solution of diisopropylethyl amine in dichloromethane was added and stirred for 1 h. The reaction was allowed to warm to ambient temperature and poured into 2N HCl and extracted with dichloromethane. The combined organic layers were washed (brine), dried ($Na_2SO_4$) and concentrated to give the virtually pure aldehyde as a pale yellow solid.

To the solution of above aldehyde in t-BuOH at 0° C. was added, an aqueous solution of TEMPO. The yellow solution was stirred at ambient temperature for 4 h and then quenched with solid ($Na_2SO_4$). The reaction mixture was acidified with HCl and extracted with dichloromethane. The combined organic phases were washed (brine), dried ($Na_2SO_4$) and concentrated. Silica gel column chromatography of the crude acid with chloroform:MeOH (9:1) gave the (S)-cyclohexylphenyl glycolic acid as a white solid. This was recrystallized from petroleum ether:ether.

Example 4

To a suspension of methyltriphenylphosphonium iodide in dry THF ambient temperature was added t-BuOK. After stirring for 15 h at ambient temperature, cyclohexylphenyl ketone was added in one portion. The reaction mixture was stirred for 8 h at ambient temperature and then quenched with aqueous ammonium chloride and extracted with ethyl acetate. The combined organic phases were washed (brine), dried ($Na_2SO_4$) and concentrated. Silica gel column chromatography of the crude product using petroleum ether:EtOAc (49.1) as eluent gave α-cyclohexylstyrene as a colorless oil.

To a mixture of $K_3Fe(CN)_6$) $K_2CO_3$ and $(DHQD)_2PHAL$ in t-BuOH—$H_2O$ (1:1) cooled to 0° C. was added OsO4 (0.1M solution in toluene). After stirring for 5 minutes at 0° C., α-cyclohexylstyrene was added in one portion. The reaction mixture was stirred at 0° C. for 18 h and then quenched with solid sodium sulfite. The stirring was continued for 1 h and the solution was extracted with ethyl acetate. The combined organic phases were washed (brine), dried ($Na_2SO_4$) and concentrated. Silica gel column chromatography of crude product using petroleum ether:EtOAc (4:1) as eluent gave (R)-1-cyclohexyl-1-phetyl-1,2-ethanediol as a white solid.

To a suspension of pyridinium dichromate in dry dichloromethane cooled at 0° C. was added a solution of (R)1-cyclohexyl-1-phenyl-,2-ethanediol in dichloromethane and stirred for 3 h. The reaction mixture was then diluted with ether and filtered. The filtrate was concentrated to give the virtually pure aldehyde as a pale yellow solid.

To the solution of above aldehyde in: t-BuOH at 0° C. was added an aqueous, solution of NaClO$_2$ and NaH$_2$PO$_4$2H$_2$O. The yellow solution was stirred at ambient temperature for 4 h and then quenched with solid Na$_2$SO3. The reaction mixture was acidified with HCl and extracted with dichloromethane. The combined organic phases were washed (brine), dried (Na$_2$SO$_4$) and concentrated. Silica gel column chromatography of the crude acid with chloroform: MeOH (9:1) gave the (R)-cyclohexylphenyl glycolic acid as a white solid. This was recrystallized from petroleum ether:ether.

Advantages of the present Invention

1. The process relatively involves less number of steps.
2. The reaction involved in each step according to the present invention, can be carried out relatively at lower temperature or ambient temperature.
3. The process leads to high yields of the desired compound.
4. Enantiomers of cyclohexylphenyl glycolic acid tan be prepared using this process.
5. The process gives high enantio-selectivity of the product
6. The chiral ligands used to induce chirality can be recovered We claim:

We claim:

1. A process for the preparation of enantiomerically pure cyclohexylphenyl glycolic acid of R or S forms, said process comprising the steps of:

a) treating cyclohexylphenyl ketone of formula (2)

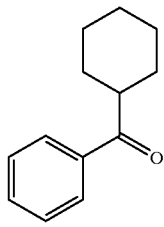

Formula (2)

with an ylide in an anhydrous solvent for a time period of 4–8 hours at an ambient temperature to obtain α-cyclohexylstyrene of formula (3);

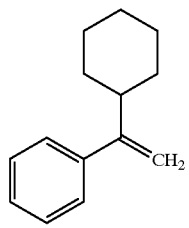

Formula (3)

b) reacting α-cyclohexylstyrene (3) obtained in step (a) with dihydroxylating agent and a chiral ligand selected from the group consisting of K$_2$CO$_3$, K$_3$Fe(CN)$_6$, phthalazine, pyrimidine phenanthryl, quinoxaline, p-chlorobenzoate and anthraquinyl groups, in t-BuOH, at a temperature range of −15° C. to an ambient temperature, for a time period of 12–18 hours, to obtain a chiral diol of formula (4);

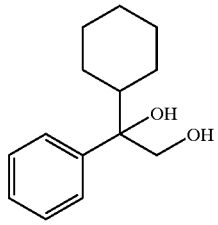

Formula (4)

c) oxidizing the primary hydroxyl group of the chiral diol (4) with an oxidizing agent in an organic solvent at a temperature range of −80° C. to −50° C. to obtain an hydroxy aldehyde; and d) oxidizing the hydroxy aldehyde of step (c) with an oxidizing agent and a buffer to obtain an enantiomerically pure cyclohexylphenyl glycolic acid of formula (1).

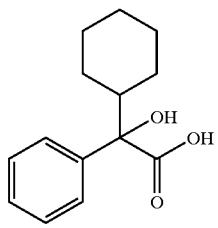

Formula (1)

2. The process of claim 1, wherein in step (a) the ylide used is generated by reacting methyltriphenylphosphonium iodide or bromide with a base at a temperature in the range of 0° C. to ambient temperature.

3. The process of claim 2, wherein step (a) the base is selected from a group consisting of n-Butyl Lithium, sodium amide, Lithium bis(trimethylsilyl) amide (SiHMDSX), Sodiumbis (trimethylsilyl) amide (NaHMDS), Potassium tertiary butoxide (t-BuOK), or Sodium hydride (NaH).

4. The process of claim 2, wherein in step (a) the base is n-butyllithium.

5. The process of claim 1, wherein in step (b) the dihydroxylating agent is osmium tetraoxide.

6. The process of claim 1, wherein in step (b) the chiral ligand controls the formation of R or S form of chiral diol.

7. The process of claim 1, wherein the chiral ligand is selected from phthalazine, pyrimidine, phenanthryl, quinoxaline, p-chlorobenzoate or anthraquinyl groups.

8. The process of claim 7, wherein the chrial ligand is phthalazine.

9. The process of claim 1, wherein in step (c) the oxidizing agent is selected from a group consisting of oxalyl chloride and DMSO, phosphorus pentoxide and DMSO, trifluoroacetic anhydride and DMSO, pyridinium chlorochromate, pyridinium dichromate, 2,2,6,6- tetramethyl 1-piperidinyloxy free radical TEMPO, or tetra-n-propylammonium perruthenate (TPAP).

10. The process of claim 9, wherein the oxidizing agent is selected from oxalyl chloride and DMSO or pyridinium chlorochromate.

11. The process of claim 10, wherein the oxalyl chloride and DMSO are in the ratio of 1.5:3.0.

12. The process of claim 1, wherein in step (c) the organic solvent is selected from chloroform and benzene.

13. The process of claim 1, wherein in step (c) the temperature at which oxidation is performed is in the range of −55 to −65° C.

14. The process of claim 1, wherein in step (d) the oxidizing agent used is selected from a group consisting of sodium chlorite, potassium chlorite, chromium trioxide in sulphuric acid or calcium chlorite.

15. The process of claim 14, wherein the oxidizing agent is sodium chlorite.

16. The process of claim 1, wherein in step (d) the buffer is selected from Sodium dihydrogen phosphate and potassium dihydrogen phosphate.

17. The process of claim 1, wherein the (R)-cyclohexylphenyl glycolic acid obtained has an enantiomeric purity up to 98%.

18. The process of claim 1, wherein the (S)-cyclohexylphenyl glycolic acid obtained has an enantiomeric purity up to 98%.

* * * * *